United States Patent [19]

Hansen et al.

[11] Patent Number: 4,999,354
[45] Date of Patent: * Mar. 12, 1991

[54] IMIDAZOQUINOXALINE COMPOUNDS AND THEIR PREPARATION AND USE

[75] Inventors: Holger C. Hansen; Frank Wätjen, both of Vaerlose, Denmark

[73] Assignee: A/S Ferrosan, Soborg, Denmark

[*] Notice: The portion of the term of this patent subsequent to Feb. 20, 2007 has been disclaimed.

[21] Appl. No.: 460,310

[22] Filed: Jan. 3, 1990

Related U.S. Application Data

[62] Division of Ser. No. 281,090, Dec. 7, 1988.

[30] Foreign Application Priority Data

Dec. 8, 1987 [DK] Denmark .............................. 6422/87

[51] Int. Cl.$^5$ ................. C07D 487/04; C07D 487/14; A61K 31/505
[52] U.S. Cl. ...................... 514/250; 544/346
[58] Field of Search .......................... 514/250; 544/346

[56] References Cited

U.S. PATENT DOCUMENTS

| | | | |
|---|---|---|---|
| 4,440,929 | 4/1984 | Lee | 544/346 |
| 4,774,245 | 9/1988 | Watjen | 514/250 |
| 4,873,244 | 10/1989 | Watjen | 544/346 |
| 4,902,686 | 2/1990 | Watjen | 544/346 |

OTHER PUBLICATIONS

Watjen II, Chem. Abs. 109, 110456e, C10-28-87.

Primary Examiner—Mark L. Berch
Attorney, Agent, or Firm—Gordon W. Hueschen

[57] ABSTRACT

New imidazoquinoxaline compounds having the general formula

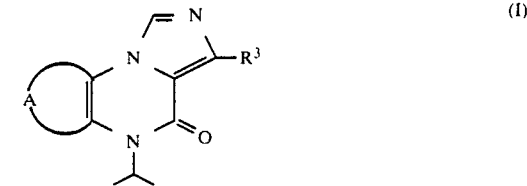

wherein
R$^3$ is

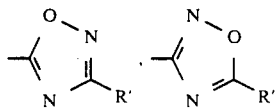

wherein
R' is C$_{1-6}$-alkyl, C$_{3-7}$-cycloalkyl or C$_{1-6}$-alkoxymethyl; and
—A— is

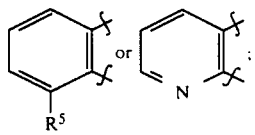

wherein
R$^5$ is hydrogen or halogen.

The compounds are useful in psychopharmaceutical preparations as anticonvulsants, anxiolytics, hypnotics, and in improving the cognitive function of the brain of mammals.

6 Claims, No Drawings

IMIDAZOQUINOXALINE COMPOUNDS AND THEIR PREPARATION AND USE

This is a division of application Ser. No. 281,090, filed Dec. 7, 1988.

The present invention relates to therapeutically active imidazoquinoxaline compounds, a method of preparing the same, pharmaceutical compositions comprising the compounds, and to methods of treating therewith. The novel compounds are useful in psychopharmaceutical applications, e.g., in the treatment of central nervous system ailments, for example, as anticonvulsants or anxiolytics.

It is well known (Squires, R. F. and Braestrup, C. in Nature (London) 266 (1977) 732-734) that specific sites in the central nervous systems of vertebrates exhibit a high specific affinity for binding 1,4- and 1,5-benzodiazepines. These sites are called benzodiazepine receptors.

It has now been found that members of a novel group of imidazoquinoxaline compounds have strong affinity for the benzodiazepine receptors which make them useful in psychopharmaceutical preparations.

Accordingly, it is an object of the invention to provide such novel imidazoquinoxaline compounds.

The imidazoquinoxaline compounds of the invention have the general formula I

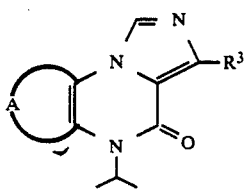

(I)

wherein
R$^3$ is

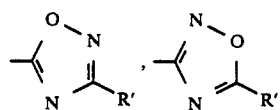

or CO$_2$R'
wherein
R' is C$_{1-6}$-alkyl, C$_{3-7}$-cycloalkyl or C$_{1-6}$-alkoxymethyl; and
—A— is

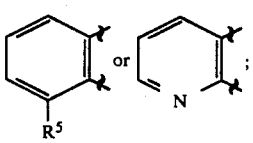

wherein
R$^5$ is hydrogen or halogen.

The invention also relates to a method of preparing the above mentioned compounds. This method comprises:

(a) reacting a compound of formula II

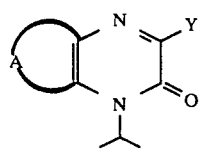

(II)

wherein —A— has the meaning set forth above and wherein Y is a leaving group, with a compound having the formula III $$CN-CH_2-R^3 \quad (III)$$

wherein R$^3$ has the meaning set forth above, to form a compound of the invention, or (b) reacting a reactive derivative of a compound having the general formula IV

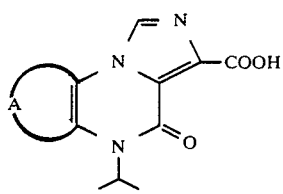

(IV)

wherein
—A— has the meaning set forth above, with a compound having the general formula V $$R'-C(=NOH)NH_2 \quad (V)$$

wherein R' has the meaning set forth above to form a compound of the general formula I wherein R$^3$ is

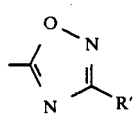

wherein R' has the meaning set forth above, or (c) reacting a compound having the general formula VI

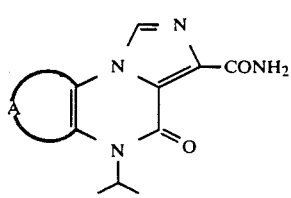

(VI)

wherein —A— has the meaning set forth above, with a compound having the general formula VII $$R'-C(OCH_3)_2N(CH_3)_2 \quad (VII)$$

wherein R' has the meaning set forth above, to form a compound having the general formula VIII

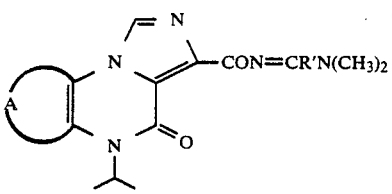

wherein —A— has the meaning set forth above and reacting the compound having the formula (VIII) with NH₂OH or another aminating agent, to form a compound having the general formula I, wherein R³ is

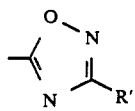

wherein R' has the meaning defined above, or (d) reacting a compound having the general formula IX

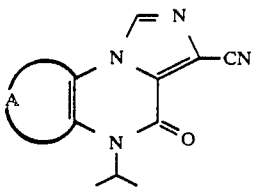

wherein —A— has the meaning set forth above, with NH₂OH to form a compound having the general formula X

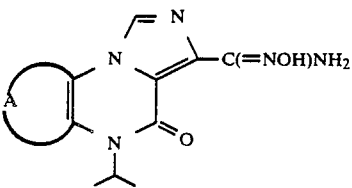

wherein —A— has the meaning set forth above, and reacting the compound having the formula (X) with R'—COCl or (R'CO)₂O wherein R' has the meaning set forth above, to form a compound of formula I, wherein R³ is

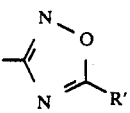

wherein R' has the meaning set forth above.

The leaving group, Y, may be any suitable leaving group and, for example, those disclosed in U.S. Pat. Nos. 4,031,079 or 4,359,420, for example, halogen, alkylthio, e.g., methylthio, aralkylthio, N-nitrosoalkylamino, alkoxy, mercapto, —OP(O)(OR)₂ wherein R is lower-alkyl or —OP(O)(NR'R'') wherein R' and R'' each represents lower-alkyl or phenyl, or together with the nitrogen atom to which they are attached represent a heterocyclic radical such as morpholino, pyrrolidino, piperidino, or methylpiperazino. The reaction is preferably carried out under alkaline conditions, i.e., in the presence of a base, and among bases alkali metal, e.g., potassium or sodium, alkoxides or hydrides are preferred. The reaction is preferably conducted in the presence of an organic solvent which is nonreactive with the reactants and products of reaction under the conditions of reaction, especially an anhydrous solvent and preferably an anhydrous aprotic solvent such as dimethylformamide (DMF) or the like. The temperature range employed may be any range suitable for the reaction to proceed at a reasonable rate and without undue delay or decomposition and a range from a minus forty (−40) degrees Celsius to about room temperature is accordingly usually particularly suitable.

The starting materials may be prepared from commercially available organic compounds and by using well known synthetic methods and as described in Synthesis, Vol. 10, pp. 681–682.

The pharmaceutical properties of the compounds of the invention can be illustrated by determining their capability for displacing radioactive labelled flunitrazepam from benzodiazepine receptors.

The displacement activity of the compounds of the invention may found by determining the $ED_{50}$ value. The $ED_{50}$ value represents the dose (mg/kg) of a test substance which causes the specific binding of flunitrazepam to benzodiazepine receptors in a living brain to be reduced to 50% of the control value.

Such an in vivo test is carried out as follows:

Principle. Twenty minutes after a doze of hu ³H-flunitrazepam ³H-FNM) (200 μCi/kg, i.v.) the amount of specific ³H-FNM binding to brain benzodiazepine receptors has reached its maximal value. This specific binding of ³H-FNM can be partly or completely prevented by simultaneous or prior administration of pharmacologically active benzodiazepines and by some benzodiazepine-like agents (Chang and Snyder, Eur. J. Pharmacol. 48, 212–218 (1978)).

Test procedure. Suspensions of test substances (2 mg/ml) are prepared in 5% Duphasol-X (TM Duphar, castor oil-ethylene oxide derivative for emulsifying and solubilizing oil and other water-insoluble substances) by sonification for 10 min using a Branson B15 microtip ultrasonifier (setting 7). Groups of three mice (female, NMR, 18–22 grams) are injected with the test substance at 100 mg/kg intraperitoneally. Fifteen minutes after test substance administration the mice are challenged with 4 μCi intravenously of ³H-FNM (70–90 Ci/mole) in 200 μl physiological saline. Twenty minutes after ³H-FNM administration mice are sacrificed by decapitation, the forebrains rapidly excised (within 30 sec) and homogenized in 12 ml of icecold 25 mM $KH_2PO_4$, pH 7.1, using an Ultra-Turrax homogenizer fitted with an N 10 shaft. Two aliquots of 1 ml are immediately filtered through Whatman GF/C glassfibre filters and washed with 2×5 ml of the above mentioned buffer. The amounts of radioactivity on the filters are determined by conventional scintillation counting. One group of untreated mice serves as control. One to three mice are injected with 25 μg/kg clonazepam i.p. 30 minutes before ³H-FNM to determine the amount of nonspecific ³H-FNM binding, which should be between 8–15% of total binding. When doses of 100 mg/kg inhibit more than 50% of specific ³H-flunitrazepam binding; test substances are administered in doses, which are factors of 3.16 times lower than 100 mg/kg. The $ED_{50}$ for a test substance is defined as that dose which inhibits 50% of specific $^3$H-FNM binding. Specific binding is the amount of binding in controls minus the amount binding in clonazepam-treated mice.

Results. The $ED_{50}$ value is determined from dose response curves. If only one dose of test substance is administered the $ED_{50}$ value is calculated as follows, provided that the inhibition of specific binding is within the range of 25-75%:

$$ED_{50} = (\text{administered dose}) \times \frac{1}{\left[\frac{C_o}{C_x} - 1\right]} \text{ mg/kg}$$

where $C_o$ is specific binding in controls and $C_x$ is specific binding in mice treated with test substance.

Test results obtained by testing some compounds of the invention will appear from the following table I.

TABLE 1

| Compound | $ED_{50}$ (mg/kg) |
|----------|-------------------|
| 3 | 0.33 |
| 6 | 0.28 |

The compound of the invention, together with a conventional adjuvant, carrier, or diluent, and if desired in the form of a pharmaceutically-acceptable acid addition salt thereof, may be placed into the form of pharmaceutical compositions and unit dosages thereof, and in such form may be employed as solids, such as tablets or filled capsules, or liquids, such as solutions, suspensions, emulsions, elixirs, or capsules filled with the same, all for oral use, in the form of suppositories for rectal administration; or in the form of sterile injectable solutions for parenteral (including subcutaneous) use. Such pharmaceutical compositions and unit dosage forms thereof may comprise conventional ingredients in conventional proportions, with or without additional active compounds or principles, and such unit dosage forms may contain any suitable effective central nervous system ailment alleviating amount of the active ingredient commensurate with the intended daily dosage range to be employed. Tablets containing one (1) milligram of active ingredient or, more broadly, one (1) to thirty (30) milligrams, per tablet, are accordingly suitable representative unit dosage forms.

The compounds of this invention can thus be used for the formulation of pharmaceutical preparations, e.g., for oral and parenteral administration to mammals including humans in accordance with conventional methods of galenic pharmacy.

Conventional excipients are such pharmaceutically acceptable organic or inorganic carrier substances suitable for parenteral or oral application which do not deleteriously react with the active compound.

Examples of such carriers are water, salt solutions, alcohols, polyethylene glycols, polyhydroxyethoxylated castor oil, gelatin, lactose, amylose, magnesium stearate, talc, silicic acid, fatty acid monoglycerides and diglycerides, pentaerythritol fatty acid esters, hydroxymethylcellulose and polyvinylpyrrolidone.

The pharmaceutical preparations can be sterilized and mixed, if desired, with auxilliary agents, such as lubricants, preservatives, stabilizers, wetting agents, emulsifiers, salt for influencing osmotic pressure, buffers and/or coloring substances and the like, which do not deleteriously react with the active compound.

For parenteral application particularly suitable are injectable solutions or suspensions, preferably aqueous solutions with the active compound dissolved in polyhydroxylated castor oil.

Ampoules are convenient unit dosage forms.

For oral application, particularly suitable are tablets, dragees, or capsules having talc and/or a carbohydrate carrier or binder or the like, the carrier preferably being lactose and/or corn starch and/or potato starch. A syrup, elixir or like can be used when a sweetened vehicle can be employed. Generally, as to broader ranges, the compounds of the invention are dispensed in unit dosage form comprising 0.05-100 mg in a pharmaceutically-acceptable carrier per unit dosage.

A typical tablet which may be prepared by conventional tabletting techniques contains:

| | |
|---|---|
| Active compound | 1.0 mg |
| Lactosum | 67.8 mg Ph.Eur. |
| Avicel ® | 31.4 mg |
| Amberlite ® IRP 88 | 1.0 mg |
| Magnesii stearas | 0.25 mg Ph.Eur. |

Due to their high degree of affinity for the benzodiazepin receptors, the compounds of the invention are extremely useful in the treatment of central nervous system ailments or disorders, when administered in an amount effective for the alleviation, amelioration, or elimination thereof. The important CNS activity of the compounds of the invention includes both anticonvulsant and anxiolytic activities along with a low toxicity, together presenting a most favorable therapeutic index. The compounds of the invention may accordingly be administered to a subject, e.g., a living animal body, including a human, in need of the same for the treatment, alleviation, amelioration, or elimination of an indication, associated with the central nervous system and the socalled benzodiazepin receptors, which requires such psychopharmaceutical treatment, e.g., especially convulsion and/or anxiety states, if desired in the form of a pharmaceutically-acceptable acid addition salt thereof (such as the hydrobromide, hydrochloride, or sulfate, in any event prepared in the usual or conventional manner, e.g., evaporation to dryness of the free base in solution together with the acid), ordinarily concurrently, simultaneously, or together with a pharmaceutically-acceptable carrier or diluent, especially and preferably in the form of a pharmaceutical composition thereof, whether by oral, rectal, or parenteral (including subcutaneous) route, in an effective psychopharmaceutical central nervous system ailment alleviating amount, e.g., an anticonvulsant and/or anxiolytic amount, and in any event an amount which is effective for the alleviation of such a central nervous system ailment due to their benzodiazepine receptor affinity. Suitable dosage ranges are 1-200 milligrams daily, 1-100 milligrams daily, and especially 1-30 milligrams daily depending as usual upon the exact mode administration, form in which administered, the indication toward which the administration is directed, the subject involved and the body weight of the subject involved, and the preference and experience of the physician or veterinarian in charge.

The invention will now be described in further detail with reference to the following examples:

EXAMPLE 1

3-cyclopropyl-5-isocyanomethyl-1,2,4-oxadiazole a. 3-cyclopropyl-5-formylaminomethyl-1,2,4-oxadiazole

A solution of ethyl formylaminomethyl-carboxylate (150 mmol) and cyclopropyl carboxamide oxime (100 mmol) in 100% EtOH (100 ml) was charged with Na (200 mg) and crushed molecular sieve (4Å) (10 g). The mixture thus obtained was stirred and heated to reflux for 8 hours. The mixture was cooled to room temperature, filtered through filter aid and the filtrate was evaporated in vacuo. The oily residue was partitionated into a $CHCl_3$ phase which was dried with $Na_2SO_4$ and evaporated.

3-methyl-5-formylaminomethyl-1,2,4-oxadiazole, 3-ethyl-5-formylaminomethyl-1,2,4-oxadiazole, and 3-methoxymethyl-5-formylaminomethyl-1,2,4-oxadiazole were prepared in exactly the same manner from the appropriate carboxamide oximes.

b. 3-cyclopropyl-5-isocyanomethyl-1,2,4-oxadiazole

A stirred solution of 3-cyclopropyl-5-formylaminomethyl-1,2,4-oxadiazole (60 mmol) and triethylamine (176 mmol) in $CH_2Cl_2$ (100 ml) was charged dropwise with $POCl_3$ (60 mmol) at 0° C. The mixture was then left for 30 minutes with stirring at 0° C. whereafter a solution of $Na_2CO_3$ (60 mmol) in $H_2O$ (50 ml) was added. The mixture was heated to room temperature, whereafter the organic phase was separated, dried and evaporated in vacuo. The residue was treated with ether, decanted and the solution was evaporated to give the title compound as an oil. The oil was processed without any further purification. The compound was characterized by its IR absorbtion band at 2160 $cm^{-1}$.

3-ethyl-5-isocyanomethyl-1,2,4-oxadiazole was prepared from 3-ethyl-5-formylaminomethyl-1,2,4-oxadiazole in a similar manner. IR: $cm^{-1}$:2170.

3-methyl-5-isocyanomethyl-1,2,4-oxadiazole was prepared from 3-methyl-5-formylaminomethyl-1,2,4-oxadiazole in a similar manner. IR: $cm^{-1}$:2170.

3-methoxymethyl-5-isocyanomethyl-1,2,4-oxadiazole was prepared from 3-methoxymethyl-5-formylaminomethyl-1,2,4-oxadiazole in a similar manner. IR: $cm^{-1}$: 2170.

EXAMPLE 2

5-cyclopropyl-3-isocyanomethyl-1,2,4-oxadiazol a. Formylaminomethyl-carboxamide oxime 0.55 mmol of freshly liberated hydroxylamine dissolved in 370 ml methanol was added to 53.6 g (0.638 mmol) N-formylamino-acetonitrile. An ice bath was used to keep the temperature below 20° C. during addition. The solution was allowed to stand at room temperature overnight, whereafter it was evaporated to give the title compound as pale crystals. Decomp. 104°-110° C.

b. 3-formylaminomethyl-5-ethyl-1,2,4-oxadiazole

A mixture of 35 ml ethylacetate, 20 g formylaminomethylcarboxamide oxime, 1 g sodium and 30 g of crushed molecular sieve (4Å) was refluxed in 300 ml abs. EtOH for 8 hours whereafter a further 1 g sodium was added. The reaction mixture was filtered and the filtrate was evaporated. The dark oily residue was suspended in 300 ml $CHCl_3$, filtered and the filtrate was evaporated to give the title compound as an oil. H-NMR(60 MHz, $CDCl_3$) (ppm): 1.4 (3H, t, J=8 Hz), 2.9 (2H, q, J=8 Hz) 4.55 (2H, s) ,7.8 (1H, broad-NH), 8.25 (1H, s).

The following compounds were synthesized from the appropriate ethyl esters in a similar manner:
3-Formylaminomethyl-5-methyl-1,2,4-oxadiazole. H-NMR (60 MHz, $CDCl_3$) (ppm); 2.6 (3H, s), 4.6 (2H, d, J=3 Hz), 7.4 (1H, broad-NH), 8.25 (1H, s).
3-Formylaminomethyl-5-methoxymethyl-1,2,4-oxadiazole H-NMR (60 MHz, $CDCl_3$) (ppm): 3.5 (3H, s), 4.7 (4H, s+d, J=6 Hz), 7.8 (1H, broad-NH), 8.25 (H, s).

c. 5-cyclopropyl-3-formylaminomethyl-1,2,4-oxadiazole

O-cyclopropancarbonylformylaminoethanamidoxime (M =185, 3,13 mol, 1000 g, 58%) was dissolved in demineralized tap water (900 ml).

O-cyclopropancarbonylformylaminoethanamidoxime was made by acylation of the oxime in acetone and contains triethylammonium chloride in the mol proportion 1:1.

The solution was refluxed for 4 h. It was checked by HPLC that the reaction was completed. The solution was cooled to 20° C., filtered, and the filtrate was extracted three times with 400 ml methylene chloride. The combined methylene chloride extracts were dried on sodium sulphate (120 g) at least 4 times with stirring. The sodium sulphate was removed by decanting and filtration and the filtrate was evaporated to give the title compound as an oil. H-NMR (60 MHz, $CDCl_3$) (ppm): 1.2 (4H, m), 2.8 (1H, m), 4.5 (2H, d, J=6 Hz), 7.8 (1H, broad-NH), 8.2 (1H, s).

d. 5-Cyclopropyl-3-isocyanomethyl-1,2,4-oxadiazole

A stirred solution of 5-cyclopropyl-3-formylaminomethyl-1,2,4-oxadiazole (60 mmol) and triethylamine (176 mmol) in $CH_2Cl_2$(100 ml) was charged dropwise with $POCL_3$ (60 mmol) at 0° C. The mixture was then left for 30 minutes with stirring at 0° C., whereafter a solution of $Na_2CO_3$(60 mmol) in $H_2O$ (50 ml) was added. The mixture was heated to room temperature, whereafter the organic phase was separated, dried and evaporated in vacuo. The residue was treated with ether, decanted and the solution was evaporated to give the title compound as an oil. The oil was processed without any further purification. The compound was characterized by its IR absorbtion band at 2160 $cm^{-1}$.

5-Ethyl-3-isocyanomethyl-1,2,4-oxadiazole, 5-methyl-3-isocyanomethyl-1,2,4-oxadiazole, and 5-methoxymethyl-3-isocyanomethyl-1,2,4-oxadiazole were prepared in a similar manner. All compounds were oils and were characterized by their IR stretching band at 2160 $cm^{-1}$.

EXAMPLE 3

Methoxyacetamide oxime 2.3 g of sodium in 33 ml of dry methanol was mixed with 6.55 g of hydroxylamine hydrochloride in 66 ml of dry methanol. The mixture was filtered and 7.8 g of methoxyacetonitrile was added dropwise to the filtrate. The mixture was left for 48 hours. The mixture was then cooled to 4° C. Filtration and evaporation of the filtrate give 8.7 g of the title compound.

The following compounds were synthesized from the appropriate nitriles in an analogous manner:
Acetamide oxime Propionamide oxime
Cyclopropyl carboxamide oxime
Isopropyl carboxamide oxime

EXAMPLE 4 a. N-ethoxalyl-N-isopropyl-2-nitroaniline

To a stirred ice-cooled solution of 2-isopropylamino-nitrobenzene (19.5 g, 0.1 mole) and triethylamine (15 ml, 0.11 mole) in tetrahydrofurane (THF, 200 ml) was dropwise added ethoxalyl chloride. The ice bath was removed and the mixture was heated to reflux for 3 hours. The precipitated triethylammonium chloride was filtered off and the filtrate was evaporated in vacuo to give the title compound as an oil.

In a similar manner was prepared 2-chloro-N-ethoxalyl-N-isopropyl-6-nitroaniline from 2-chloro-N-isopropyl-6-nitroaniline and ethoxalylchloride. The product was isolated as an oil.

b. 3,4-dihydro-4-isopropyl-2-hydroxy-3-oxo-quinoxaline-1-oxide

A solution of N-ethoxalyl-N-isopropyl-2-nitroaniline (28 g, 0.1 mole) in ethanol (250 ml) was charged with 5% Pd/C (1 g) and hydrogenated under standard conditions. After completion of the hydrogenation methylene chloride (200 ml) was added to dissolve the product. The Pd/C was filtered off and the filtrate was evaporated to give the title compounds as white crystals. M.p. 229°–231° C.

In a similar manner 8-chloro-1,2,3,4-tetrahydro-1-isopropyl-2,3-dioxo-quinoxaline was prepared from 2-chloro-N-ethoxalyl-N-isopropyl-6-nitroaniline by hydrogenation using methylene chloride as solvent. M.p. 228°–229° C.

c. 1,2,3,4-tetrahydro-1-isopropyl-2,3-dioxo quinoxaline

A solution of 3,4-dihydro-4-isopropyl-2-hydroxy-3-oxo-quinoxaline-1-oxid (15.5 g, 0.07 mole) and triphenylphosphine (26.2 g, 0.1 mole) in dimethylformamide (DMF) (100 ml) was stirred at 120° C. for 12 hours, whereafter the solvent was evaporated in vacuo. The residue was stirred in methylene chloride (150 ml) whereby the formed triphenyl phosphine oxid was dissolved. The product was then collected as pale crystals by filtration followed by wash with methylene chloride M.p. 227°–228° C.

d. 4-isopropyl-1,2,3,4-tetrahydro-2,3-dioxo pyrido[2,3-b]-pyrazine

To a stirred solution of 3-amino-2-isopropylamino-pyridine (2.0 g, 10.6 mmole) and triethylamine (4.8 ml, 34.6 mmole) in tetrahydrofuran (30 ml) was dropwise added ethoxalyl chloride (2.68 ml, 24 mmole). Stirring was continued for two hours after the addition. The mixture was filtered through a glass filter funnel and the filtrate was evaporated to give the title compound as white crystals. M.p. 246°–247° C.

EXAMPLE 5

Ethyl 4,5-dihydro-5-isopropyl-4-oxo-imidazo[1,5-a]quinoxaline-3-carboxylate (Compound 1)

SOLUTION A:

1,2,3,4-tetrahydro-1-isopropyl-2,3-dioxo-quinoxaline (20 g, 0.1 mole) was dissolved in dry DMF (250 ml) with stirring whereafter potassium t-butoxide (14.5 g, 0.13 mole) was added. The stirred solution was then cooled under an atmosphere of $N_2$ to $-30°$ C. whereafter diethylchlorophosphate (18.5 ml, 9.13 mole) was added. The temperature of the mixture was then allowed to rise to 10° C. before it again was cooled to $-30°$ C. and mixed with solution B.

SOLUTION B:

Potassium t-butylate (14.5 g, 0.13 mole) was dissolved in dry DMF (150 ml) with stirring at room temperature. The temperature was lowered to $-40°$ C. and ethyl isocyanomethyl carboxylate (14.3 ml, 0.13 mole) was added. After stirring for 10 min at $-40°$ C. the solution was added to solution A.

The final mixture was stirred for 30–60 min without any external cooling. Acetic acid was added to neutralize the excess of base, before removal of the DMF by evaporation in vacuo.

The dark oily residue was then treated with $H_2O$/EtAC - 100 ml/30 ml. This afforded precipitation of crude product as pale crystals.

Content of starting material in the crude product was removed by extraction of a $CH_2Cl_2$ solution with 4N NaOH. Final yield 19.8 g. M.p. 158°–159° C.

In a similar manner 4,5-dihydro-5-isopropyl-3-(5-methyl-1,2,4-oxadiazol-3-yl)-4-oxo-imidazo[1,5-a]quinoxaline m.p. 214°–215° C. was prepared from 1,2,3,4-tetrahydro-1-isopropyl-2,3-dioxo-quinoxaline and 3-isocyanomethyl-5-methyl-1,2,4-oxadiazole. (Compound 2)

Likewise 3-(5-cyclopropyl-1,2,4-oxadiazol-3-yl)-4,5-dihydro-5-isopropyl-4-oxo-imidazo[1,5-a]quinoxaline, m.p. 168°–170° C. was prepared from 1,2,3,4-tetrahydro-1-isopropyl-2,3-dioxo-quinoxaline and 3-isocyanomethyl-5-cyclopropyl-1,2,4-oxadiazole. (Compound 3)

Likewise 6-chloro-3-(5-cyclopropyl-1,2,4-oxadiazol-3-yl)-4,5-dihydro-5-isopropyl-4-oxo-imidazo[1,5-a]quinoxaline m.p. 219°–221° C. was prepared from 5-chloro-1,2,3,4-tetrahydro-1-isopropyl-2,3-dioxo-quinoxaline and 5-cyclopropyl-3-isocyanomethyl-1,2,4-oxadiazole. (Compound 4)

Likewise ethyl 4,5-dihydro-5-isopropyl-4-oxo-imidazo[1,5-a]pyrido[2,3-e]pyrazine-3-carboxylate. M.p. 176°–177° C. was prepared from 4-isopropyl-1,2,3,4-tetrahydro-2,3-dioxo-pyrido[2,3-b]pyrazine and ethyl isocyanoacetate. (Compound 5)

EXAMPLE 6

3-(3-cyclopropyl-1,2,4-oxadiazol-5-yl)-4,5-dihydro-5-isopropyl-4-oxo-imidazo[1,5-a] quinoxaline A mixture of ethyl 4,5-dihydro-5-isopropyl-4-oxo-imidazo[1,5-a] quinoxaline-4-carboxylate (3 g), cyclopropylcarboxamidoxime (5 g) and crushed mol. sieves 4 Å (6–10 g) was added to 100% EtOH (50 ml) wherein Na (200 mg) previously had been dissolved. The mixture was stirred at reflux temperature for 2 hours whereafter it was cooled to room temperature and charged with $CH_2CL_2$ (50 ml) in order to dissolve any precipitated product, after filtration through a pad of filter aid the filtrate was reduced to a volume of ca. 15 ml by evaporation in vacuo. Water (50 ml) was then added to the reduced filtrate. This afforded precipitation of the title compound as white crystals yield upon filtration 2.7 g. M.p. 206°–207° C. (Compound 6)

In a similar manner 4,5-dihydro-5-isopropyl-3-(3-methyl-1,2,4-oxadiazol-5-yl)-4-oxo-imidazo[1,5- a]quinoxaline m.p. 222°-223° C. was prepared by reaction between ethyl 4,5-dihydro-5-isopropyl-4-oxo-imidazo[1,5-a]quinoxaline-3-carboxylate and methylcarboxamide oxime. (Compound 7)

Likewise 4,5-dihydro-5-isopropyl-3-(3-methoxymethyl-1,2,4-oxadiazol-5-yl)-4-oxo-imidazo[1,5-a]quinoxaline m.p. 195°-196° C. was prepared by reaction between ethyl-4,5-dihydro-5-isopropyl-4-oxo-imidazo[1,5-a]quinoxaline-3-carboxylate and methoxymethyl carboxamidoxime. (Compound 8)

Likewise 3-(3-cyclopropyl-1,2,4-oxadiazol-5-yl)-4,5-dihydro-5-isopropyl-4-oxo-imidazo-[1,5-a]pyrido[2,3-e]pyrazine m.p. 221°-223° C. was prepared by reaction between ethyl 4,5-dihydro-5-isopropyl-4-oxo-imidazo[1,5-a]pyrido[2,3-e]pyrazine and cyclopropyl carboxamidoxime. (Compound 9)

I claim:

1. Imidazoquinoxaline compounds having the formula I

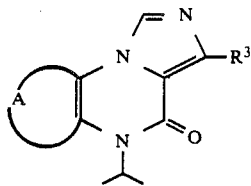
(I)

wherein
R³ is

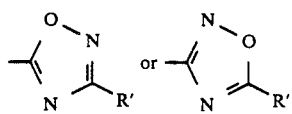

wherein

R' is C₁₋₆-alkyl, C₃₋₇-cycloalkyl or C₁₋₆-alkoxymethyl; and
—A— is

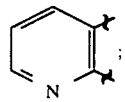

2. A compound of claim 1 which is 3-(3-cyclopropyl-1,2,4-oxadiazol-5-yl)-4,5-dihydro-5-isopropyl-4-oxo-imidazo[1,5-a]-pyrido(2,3-e)pyrazine.

3. A pharmaceutical composition suitable for use in the treatment of a central nervous system ailment associated with the benzodiazepine receptors selected from convulsions and anxiety comprising an amount of a compound of claim 1 which is effective for the alleviation of such disorder together with a pharmaceutically-acceptable carrier or diluent.

4. A pharmaceutical composition according to claim 3 wherin it is in the form af an oral dosage unit containing 1-100 mg of the active compound.

5. A method of treating a central nervous system ailment associated with the benzodiazepine receptors selected from convulsions and anxiety in a subject in need of such treatment comprising the step of administering to said subject an amount af a compound of claim 1 which is effective for the alleviation of such ailment.

6. A method of treating a central nervous system ailment associated with the benzodiazepine receptors selected from convulsions and anxiety in a subject in need of such treatment comprising the step of administering to said subject an amount af a compound of claim 1 which is effective for the alleviation of such ailment in the form af a pharmaceutical composition thereof, in which it is present together with a pharmaceutically-accpetable carrier or diluent.

* * * * *

UNITED STATES PATENT AND TRADEMARK OFFICE
CERTIFICATE OF CORRECTION

PATENT NO. : 4,999,354

DATED : Mar. 12, 1991

INVENTOR(S) : Holger C. Hansen, Frank Wätjen

It is certified that error appears in the above-identified patent and that said Letters Patent is hereby corrected as shown below:

Column 1, line 6; change the period to a comma -- , -- after "1988", and add -- now U.S. Pat. No. 4,968,682, issued Nov. 6, 1990. --.

Column 4, approximately line 31; "doze of hu 3H-" should read -- dose of $^3$H- --.

Column 4, line 32; "flunitrazepam $^3$H-FNM)" should read -- flunitrazepam ($^3$H-FNM) --.

Column 5, line 67; "application particularly" should read -- application, particularly --.

Column 6, line 39; "socalled" should read -- so-called --.

Column 6, approximately line 61; "mode administration," should read -- mode of administration, --.

Column 7, approximately line 28; "C. where-" should read -- C., where- --.

Column 8, approximately line 40; "POCL$_3$" should read -- POCl$_3$ --.

Column 12, approximately line 22; "wherin" should read -- wherein--.
Column 12, approximately line 22; "af" should read -- of --.
Column 12, approximately line 28; "af" should read -- of --.
Column 12, approximately line 34; "af" should read -- of --.
Column 12, approximately line 36; "af" should read -- of --.
Column 12, approximately line 38; "accpetable" should read -- acceptable --.

Signed and Sealed this

Twenty-second Day of September, 1992

*Attest:*

DOUGLAS B. COMER

*Attesting Officer*     *Acting Commissioner of Patents and Trademarks*